United States Patent [19]
Bigge et al.

[11] Patent Number: 5,942,513
[45] Date of Patent: Aug. 24, 1999

[54] PHARMACEUTICAL COMPOSITION AND A METHOD FOR TREATING NEURODEGENERATIVE DISEASES USING A COMBINATION OF A KAINATE EXCITATORY AMINO ACID ANTAGONIST AND AN URICOSURIC AGENT

[75] Inventors: Christopher Franklin Bigge; Graham Johnson, both of Ann Arbor; Charles Price Taylor, Jr., Chelsea; Devin Franklin Welty, Ann Arbor, all of Mich.

[73] Assignee: Warner-Lambert Company, Morris Plains, N.J.

[21] Appl. No.: 09/049,495

[22] Filed: Mar. 27, 1998

Related U.S. Application Data

[62] Division of application No. 08/775,637, Dec. 31, 1996, Pat. No. 5,767,119, which is a division of application No. 08/539,398, Oct. 5, 1995, Pat. No. 5,627,168, which is a division of application No. 08/285,381, Aug. 3, 1994, abandoned, which is a division of application No. 08/049,228, Apr. 19, 1993, Pat. No. 5,407,935, which is a continuation of application No. 07/756,401, Sep. 9, 1991, abandoned.

[51] Int. Cl.$^6$ ............ A61K 31/495; A61K 31/50
[52] U.S. Cl. ............ 514/250; 514/249; 514/255
[58] Field of Search ............ 514/249, 250, 514/255

[56] References Cited

PUBLICATIONS

CA 103:98585, Chapman et al., 1985.
CA 121:252922, Rocamora et al., 1994.
CA 127:157079, Matheus et al., 1997.

*Primary Examiner*—Kimberly Jordan
*Attorney, Agent, or Firm*—Todd M. Crissey

[57] ABSTRACT

The present invention relates to a pharmaceutical composition containing a kainate excitatory amino acid antagonist and an uricosuric agent and to a method of treating neurodegenerative diseases using a combination of a kainate excitatory amino acid antagonist and an uricosuric agent.

10 Claims, 4 Drawing Sheets

PHARMACEUTICAL COMPOSITION AND A METHOD FOR TREATING NEURODEGENERATIVE DISEASES USING A COMBINATION OF A KAINATE EXCITATORY AMINO ACID ANTAGONIST AND AN URICOSURIC AGENT

CROSS-REFERENCE TO RELATED APPLICATIONS

This application is a divisional of U.S. application Ser. No. 08/775,637, filed Dec. 31, 1996, now U.S. Pat. No. 5,767,119, which is a divisional of U.S. application Ser. No. 08/539,398, filed Oct. 5, 1995, now U.S. Pat. No. 5,627,168, which is a divisional of U.S. application Ser. No. 08/285,381, filed Aug. 3, 1994, abandoned, which is a divisional of U.S. application Ser. No. 08/049,228, filed Apr. 19, 1993, now U.S. Pat. No. 5,407,935, which is a file wrapper continuation of U.S. application Ser. No. 07/756,401, filed Sep. 9, 1991, abandoned.

BACKGROUND OF THE INVENTION

The present invention is a pharmaceutical composition and method for coadministration of a uricosuric agent and the like, such as probenecid or sulfinpyrazone and an excitatory amino acid (EAA) antagonist, including, for example, an AMPA antagonist, a strychnine insensitive glycine antagonist, or a competitive NMDA antagonist. This invention results in a significant increase in the duration of action and magnitude of effect for such EAA antagonists.

Numerous excitatory amino acid antagonists have been described which potently inhibit the activation of both N-methyl-D-aspartate (NMDA) and AMPA and kainic acid receptor associated ion channels in vitro. However, in vivo activity in a range of pharmacological models has often been shown to be significantly less than expected from a knowledge of the in vitro receptor binding profile. This diminished in vivo activity is thought to result from limited access of these compounds to the brain resulting from an inability to pass passively through the blood brain barrier (BBB). Poor blood brain barrier permeability has often been observed or inferred for polar or hydrophilic compounds (see, for example, R. P. Compton, et al, in *Neuroscience Letters* 84:339–344 (1988) and A. G. Chapman, et al, in *Neuroscience Letters* 37:75–80 (1983). However, in addition to an inability to cross the blood brain barrier, the inability to establish a sufficient concentration of a pharmacological agent in the brain may also result from the existence of unidirectional transport systems which are known to exist in the luminal wall of the endothelial cells which comprise the blood brain barrier. See R. Spector, in Pharmacology 40:1–7 (1990). The suggested endogenous function of such transport systems is to remove unwanted biological molecules and metabolic byproducts from the cerebrospinal fluid surrounding the brain. However, in the case of a desirable pharmacological agent, such transport systems may instead act to limit inappropriately the access of such compounds into the brain. The result of this situation is that to achieve sufficient brain concentrations of such pharmacological agents necessary for the desired pharmacological effect to be observed, compounds are required to be given in higher doses and at more frequent intervals. This increased brain penetration is often achieved through elevating serum drug concentrations to the point where significant peripheral side effects or organ toxicity are evident. Compounds which would act to inhibit the operation of such unidirectional brain endothelial transport systems would therefore be predicted to reduce the amount of a pharmacological agent required to elicit a pharmacological effect in addition to prolonging its duration of action. Such a reduction in required dosing would, of course, minimize the occurrence of peripheral side effects and limit specific organ toxicity.

Much is known about the effects; such as on renal excretion, of uricosuric drugs (see Gutman, "Uricosuric Drugs, with Special Reference to Probenecid and Sulfinpyrazone", *Advances in Pharmacology* 4:91–142 (1966)) and particularly probenecid (see Beyer, "Factors Basic to the Development of Useful Inhibitors of Renal Transport Mechanisms," *Arch. Int. Pharmacodyn.* XCVII (1):97–117 (1954); Weiner, et al, "On the Mechanism of Action of Probenecid on Renal Tubular Secretion," *Bull. Johns Hopkins Hospital* 156:333–346 (1960); Hedaya, et al, "Probenecid Inhibits the Metabolic and Renal Clearances of Zidorudine (AZT) in Human Volunteers", *Pharmac. Res.* 7(4):411–417 (1990), and "Probenecid", Goodman and Gilman, 8th ed. pp 745–746).

In fact, generally, Cunningham, et al, in "Clinical Pharmacokinetics of Probenecid", *Clinical Pharmacokinetics* 6:135–151 (1981) stated "Most of the drug-drug interactions involving probenecid are due to an effect on the kidney block of transport of acidic drugs."

As early as 1950 another effect of probenecid was recognized on paraaminosalicylic acid and penicillin (see Boger, et al, "The Influence of a New Benzoic Acid Derivative of the Metabolism of Paraaminosalicylic Acid (PAS) and Penicillin" as presented before the 31st Annual Session of the American College of Physicians, Boston, April, 1950). Other disclosures of the effects of probenecid are found as follows:

Gibaldi, et al, "Apparent Effect of Probenecid on the Distribution of Penicillins in Man", *Clinical Pharmacology and Therapeutics* 9(3):345–349; Dewhurst, K., "The Use of Probenecid for Increasing Penicillin Concentrations in Cerebro-Spinal Fluid", *Acta Neurol. Scandinav.* 45:253–256 (1969); Sjöström, R., "Steady-State Levels of Probenecid and Their Relation to Acid Monamine Metabolites in Human Cerebrospinal Fluid", *Psychopharmacologia* (Berl.) 25:96–100 (1972).

Spector, R. and Lorenzo, A. V., "The Effects of Salicylate and Probenecid on the Cerebrospinal Fluid Transport of Penicillin, Aminosalicylic Acid and Iodide", *The Journal of Pharmacology and Experimental Therapeutics* 1988(1):55–65 (1974); Roos, et al, "Quantitation of CSF Concentrations and Biological Activity of Probenecid Metabolites", *Eur. J. Clin. Pharmacol.* 17:223–226 (1980); Van Der Poel, F. W., et al, "Evidence for a Probenecid-Sensitive Transport System of Acid Monoamine Metabolites from the Spinal Subarachnoid Space", *Psychopharmacology* 52:35–40 (1977); Bode, et al, "Active Transport of Methotrexate from Cerebrospinal Fluid in Humans", *Cancer Research* 40:2184–2187 (July 1980); Hedaya, M. A. and Sawchuk, R. J., "Effect of Probenecid on the Renal and Nonrenal Clearances of Zidovudine and its Distribution into Cerebrospinal Fluid in the Rabbit, *J. of Pharmaceutical Sciences* 78(9):716–22 (September 1989); Sawchuk, R. J. and Hedaya, M. A., "Modeling the Enhanced Uptake of Zidovudine (AZT) into Cerebrospinal Fluid. I. Effect of Probenecid, *Pharmaceutical Research* 7(4):332–338 (1990).

Studies regarding excitatory amino acid antagonist pharmacokinetics provide no basis to lead an ordinary artisan to the differences of the present invention. See Chapman, et al, "Uptake of a Novel Anticonvulsant Compound, 2-Amino-7-Phosphono-[4,5-$^3$H]Heptanoic Acid, into Mouse Brain", *Neuroscience Letters* 37:75–80 (1983) and Compton, et al, "Determination of the Pharmacokinetics of 2-Amino-7-Phosphonoheptanoate in Rat Plasma and Cerebrospinal Fluid", *Neuroscience Letters* 84:339–344 (1988).

Specifically, I. McDonald of Merrell-Dow presented a talk at the Excitatory Amino Acid Symposium held at the American Chemical Society Spring National Meeting held in Atlanta, Ga. on Apr. 15, 1991 in which he stated that preliminary metabolic studies show longer duration of protection against seizures induced by quinolinic acid in mice when pretreated with probenecid followed by the administration of a compound of the formula 4-[(carboxymethyl) imino]-5,7-dichloro-1,4-dihydro-2-quinolinecarboxylic acid (MDL 100,748), This was shown by the following data:

Preliminary Metabolic Studies

4-[(Carboxymethyl)imino]-5,7-dichloro-1,4-dihydro-2-quinolinecarboxylic Acid (MDL 100,748)

Effect of MDL 100,748 (65 mg/kg; IV) in the quinolinic acid seizure model in mice.

| Time of Administration of MDL 100,748 Prior to QA | Protection |
| --- | --- |
| 5 min | 9/10 |
| 30 min | 0/10 |

Mice pretreated (30 min) with probenecid 200 mg/kg (IP) 30 minutes prior to receiving 65 mg/kg (IV) of MDL 100,748.

| Time of Administration of MDL 100,748 Prior to QA | Protection |
| --- | --- |
| 5 min | 9/10 |
| 30 min | 7/10 |

However, the prolonged protection provided by probenecid described in the talk was attributed to the reduced metabolism resulting from inhibition of renal transport mechanisms. This differs from the present invention now found to provide reduced amounts of antagonist for effects equivalent to previously known larger amounts.

The present invention differs from the oral disclosure as it is based on prevention of the unilateral transport of EAA acid competitive NMDA antagonists from brain to blood by coadministration of probenecid and related compounds. In other words, the method of the present invention prolongs the effect of these antagonists by interfering with the efflux of the antagonists from the site of their activity, not inhibition of renal excretion.

The coadministration of the present invention is different from that expected by an ordinarily skilled artisan from the above-noted disclosures. It is now found that the predominant pharmacokinetic effect of probenecid on the EAA and competitive NMDA antagonists in the present method of coadministration is based on the previously unappreciated unidirectional effect on the antagonists in relation to the blood brain barrier. Generally, Kang, et al, "Acidic Drug Transport In Vivo Through the Blood-Brain Barrier. A Role of the Transport Carrier for Monocarboxylic Acids", in *J. Pharmacobio-Dyn.*, 13:158–163 (1990) teach "acidic drugs could be transported by a carrier-mediated system for monocarboxylic acids at the BBB (blood brain barrier) and the transport system was not changed by the disease state."

Further, Oldendorf, W. in "Certain Aspects of Drug Distribution to Brain", (1976) provides a discussion of differing elements of blood brain barrier permeability describing a flow-limited distribution. It is now found the present method of coadministration provides a positive effect on the availability of EAA antagonists in the brain contrary to the flow-limited distribution for antagonist administration alone.

Certainly no predictability regarding the results of coadministration of the present invention method is previously shown.

SUMMARY OF THE INVENTION

The present invention is a method of treating a disease advantageously affected by an EAA antagonist in a human suffering therefrom comprising coadministration of a uricosuric agent, preferably probenecid, and (1) an EAA antagonist. The amount of agent and the amount of antagonist is an optimally effective amount of each when administered together for the treatment of the disease.

The present invention is a pharmaceutical composition for treating a disease advantageously affected by an excitatory amino acid antagonist which comprises an amount of probenecid effective to inhibit unidirectional efflux of an amount of the excitatory amino acid antagonist from the brain effective for the treatment of the disease the amount of the excitatory amino acid together with a pharmaceutically acceptable carrier.

The present invention is a method for treating a disease advantageously affected by an excitatory amino acid antagonist in a human suffering therefrom comprising the above pharmaceutical composition in unit dosage form.

The present invention is also a method for the manufacture of a pharmaceutical composition for treating a disease advantageously affected by an excitatory amino acid antagonist which is an amount of probenecid effective to inhibit efflux from the brain of the antagonist consisting of an excitatory amino acid antagonist and the effective amount of the antagonist to treat the neurodegenerative disease together with a pharmaceutically acceptable carrier.

The present invention is a composition and a method for treatment of neurodegenerative disorders.

Excessive excitation by neurotransmitters can cause the degeneration and death of neurons. It is believed that this degeneration is in part mediated by the excitotoxic actions of the excitatory amino acids (EAA), particularly of glutamate and aspartate at N-methyl-D-aspartate (NMDA), α-amino-3-hydroxy-5-methyl-isoxazole propionic acid (AMPA), and kainate receptors This excitotoxic action is responsible for the loss of neurons in cerebrovascular disorders such as cerebral ischemia or cerebral infarction resulting from a range of conditions such as thromboembolic or hemorrhagic stroke, cerebral vasospasm, hypoglycemia, cardiac arrest, status epilepticus, perinatal asphyxia, anoxia such as from drowning, pulmonary surgery and cerebral trauma as well as lathyrism, Alzheimer's, and Huntington's diseases. These compounds may also be useful for the treatment of schizophrenia, epilepsy, anxiety, pain, drug addiction, and emesis.

Suggested therapies for these neurodegenerative diseases include compounds which act specifically as antagonists of EAA receptors and in particular the NMDA receptor (Schwarz, R. and Meldrum, B., *The Lancet* 140 (1985); Meldrum, B. in "Neurotoxins and Their Pharmacological Implications", edited by P. Jenner, Raven Pres, New York (1987); Choi, D. W., Neuron 1:623 (1988).

The disease advantageously affected by excitatory amino acid antagonists of the present composition and method of use generally includes a disorder responsive to an excitatory amino acid antagonist including, for example, disorders characterized as neurodegenerative. Such diseases or disorders include what are commonly known as stroke, convulsions, migraines or senility but more particularly result from cerebral ischemia; cerebral infarction; cerebral vasospasm; hypoglycemia; cardiac arrest; status epilepticus or cerebral trauma. Conditions also responsive to excitatory amino acid antagonists include; schizophrenia; epilepsy; pain; anxiety; neurodegenerative disorders such as Alzheimer's disease; Huntington's disease; or control of emesis. Diseases preferably treated with an excitatory amino acid antagonist are: convulsions or epilepsy or stroke.

BRIEF DESCRIPTION OF THE DRAWINGS

The drawings consist of FIGS. 1, 2, 3, and 4.

DETAILED DESCRIPTION

Figure 1:
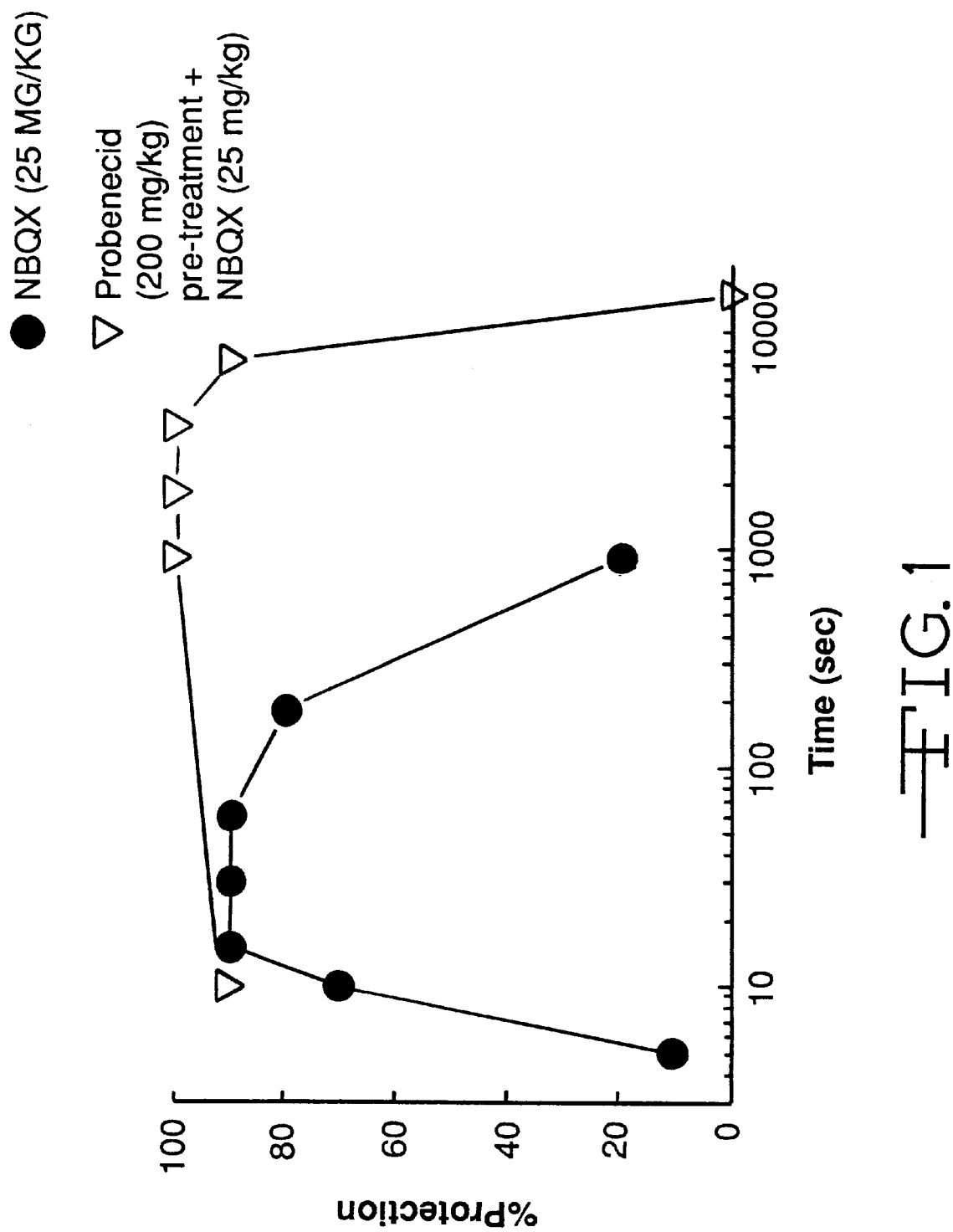
FIG. 1 shows the effect of anticonvulsant action over time of 25 mg/kg of 2,3-dihydroxy-6-nitro-7-sulfamoyl-benzo(F)quinoxaline, NBQX, administered by intravenous injection, identified hereinafter, in 10 mice as ● and the effect of anticonvulsant action over time of 25 mg/kg of NBQX also administered by intravenous injection in mice pretreated (30 minutes before injection of NBQX) by intraperitoneal injection of 200 mg/kg of probenecid ▽.

The excitatory amino acid antagonist of the composition and method of the present invention include each of the compounds of the following patents or applications which are incorporated by reference therefor:

I. Quinoxaline diones in EP 377,112-A; EP 374534-A; EP 348872-A; EP 315959-A; EP 260467-A; U.S. Pat. No. 4,889,855; and U.S. Pat. No. 4,812,458;

II. Quinoxalinic acid derivatives in U.S. application Ser. Nos. 624,156 filed Dec. 7, 1990; and 631,139 filed Dec. 20, 1990;

III. Indole derivatives in the following patents and copending applications:

U.S. Pat. Nos. 4,960,786, EP 396124, and U.S. application Ser. Nos. 670,860 filed Mar. 18, 1991; 699,875 filed May 14, 1991, and 705,022 filed May 24, 1991;

IV. Kynurenic acid derivatives:
EP 38E;839-A and EP 303387;

V. Pyrrolidinone derivatives:
U.S. Pat. No. 4,925,867, U.S. Pat. No. 4,863,953, and GB 2231048-A;

VI. D-cycloserine, its prodrugs and admixtures with other compounds in:
EP 387867, EP 378134, and U.S. Pat. No. 4,904,681;

VII. Isatine derivatives in:
U.S. application Nos. 624,157 filed Dec. 7, 1990; 624,409 filed Dec. 7, 1990, and 670,061 filed Mar. 15, 1991; also Ref. No. NS12.

The competitive NMDA antagonist of the composition and method of the present invention include each of the compounds of the following patents or applications which are incorporated by reference therefor:

GB2104078-A; EP 420806-A, EP 391850, U.S. Pat. No. 4,906,621, U.S. Pat. No. 4,898,854, EP 302826-A, U.S. Pat. No. 4,746,653, EP 275820, U.S. Pat. No. 4,705,781, U.S. Pat. No. 4,968,678, U.S. Pat. No. 4,902,687, U.S. application Ser. No. 902,695, EP 418863-A; U.S. Pat. No. 4,761,405, U.S. Pat. No. 4,657,899; Parke-Davis: Applications as follows: GB 2157685-B; GB 2198134-B, GB 2201676-A, GB 2156818-B; U.S. Pat. No. 4,918,064, EP 364996-A, EP 342558.

Effects of each of the above-noted antagonists (EAA, including, for example, an AMPA antagonist, a strychnine insensitive glycine antagonist, or competitive NMDA antagonist) are centrally mediated by the uricosuric agent, preferably probenecid in the method of the present invention so that the effects of each of the compounds is extended and its effectiveness increased per dose of antagonist without increased side effects. These effects are due to higher amounts of the antagonists of the present invention in the brain because probenecid inhibits unidirectional transport from the brain. Clearly this differs from inhibition of renal excretion as set out in the oral disclosure above since such inhibition of excretion would be understood to increase blood levels of the antagonists throughout the body. Under this rationale, the antagonist-induced peripheral side effects would be expected to increase when combined with probenecid rather than as in the present invention provide for a lower dose of probenecid for greater effectiveness at the same time minimizing peripheral side effects.

Preferred combinations of the present invention include NBQX and probenecid; and CPP and probenecid.

According to this invention a combination of either an EAA antagonist or a competitive NMDA antagonist and preferably probenecid is administered in an amount effective to treat a neurodegenerative disease.

The combination comprises a daily dose of an uricosuric agent of about 1 g/day to 4 g/day and preferably about 2 g/day of probenecid. This may be given in four divided portions of 500 mg/dose (see Goodman and Gilman, "Probenecid", 8th Ed., pages 745–746; Selen, et al, "Pharmacokinetics of Probenecid Following Oral Doses of Human Volunteers", *J. of Pharma. Sci.* 71(11) (November 1982); and Selen, A., "Dose Dependent Pharmacokinetics of Probenecid. Following Single and Repeated Doses", a thesis for the degree of Doctor of Philosophy from the University of Wisconsin-Madison.

For the EAA antagonists of the present invention the combination also comprises an amount of antagonist which is approximately tenfold less than for antagonist alone for comparable activity in the treatment of the neurodegenerative disease. For example, for NBQX alone (defined hereinafter), the dosage range is from 0.1 mg/kg to 1 mg/kg with a daily dose from 0.5 mg/kg/day to 5.0 mg/kg/day totally but for the present invention the dosage is from 0.01 mg/kg up to less than 0.1 mg/kg, with a daily dose from 0.02 mg/kg/day to 0.2 mg/kg/day such that NBQX need only be given twice daily rather than 4 to 5 times daily.

For a competitive NMDA antagonist of the present invention the combination also comprises an amount of antagonist which is approximately twofold less than for antagonist alone. For example, for CPP alone the dosage range is from 0.03 mg/kg to 0.30 mg/kg with a daily dose of from 0.10 mg/kg/day to 1.0 mg/kg/day totally but for the present invention the dosage is from 0.015 mg/kg up to but not including 0.15 mg/kg with a daily dose from 0.05 mg/kg/day to 0.5 mg/kg,/day.

The pharmaceutical compositions of the invention can take any of a wide variety of oral and parenteral dosage forms. The dosage forms comprise as the active components an antagonist; either an EAA antagonist or a competitive NMDA antagonist, as defined previously and an uricosuric agent preferably probenecict as defined previously.

For preparing pharmaceutical compositions, one uses inert, pharmaceutically acceptable carriers that can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compounds. In the tablet, the active compounds are mixed with carrier having the necessary binding properties in suitable proportions and compacted in the shape and size desired. The powders and tablets preferably contain from 5% or 10% to about 70% of active ingredients. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compounds with encapsulating materials as carrier, providing a capsule in which the active components (with or without other carriers) are surrounded by carrier, which are thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active components in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation may be subdivided into unit doses containing appropriate quantities of antagonist and probenecid individually or as a combination, i.e., in a mixture. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form. Additionally, the unit dosage form may be a dividable form having antagonist in one part and probenecid in the other part, such as, a dividable capsule, a dividable package, or a two-part ampoule, vial or the like.

The quantity of antagonist and probenecid in a unit dose of preparation may be varied or adjusted from about 0.01 mg/kg to 10.0 mg/kg, preferably 0.03 mg/kg to less than 0.1 mg/kg of antagonist together with about 500 mg to 2000 mg of uricosuric agent, preferably about 500 mg of probenecid, according to the particular application and the potency of the active ingredients.

The pharmaceutical compositions preferably are constituted so that they can be administered parenterally or orally. Solutions of the active compounds as free bases and free acids or pharmaceutically acceptable salts can be prepared in water suitable mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion, and by the use of surfactants. The prevention of the action of microorganisms can be brought about by various antibacterial and antifungal agents, for example, paragens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients, into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of active ingredients plus an additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active materials calculated to produce the desired therapeutic effect in association with the required pharmaceutical carrier. The specification for the novel dosage unit forms of the invention are dictated by and directly dependent on (1) the unique characteristics of the active materials and the particular therapeutic effect to be achieved, and (b) the limitation inherent in the art of compounding such active materials for the treatment of disease in living subjects having a diseased condition in which bodily health is impaired as herein disclosed in detail.

The principal active ingredients are compounded for convenient and effective administration in effective amounts with a suitable pharmaceutically acceptable carrier in dosage unit form as hereinbefore disclosed. A unit parenteral dosage form can, for example, contain the principal active compound, i.e. EAA antagonist, in amounts ranging from about 0.5 to about 100 mg, with from about 0.1 to 50 mg being preferred in combination with about 500 mg of probenecid. The daily parenteral doses for mammalian subjects to be treated ranges from 0.01 mg/kg to 10 mg/kg of the EAA antagonist. The preferred daily dosage range is 0.1 mg/kg to 1.0 mg/kg.

The antagonists described above may form commonly known, pharmaceutically acceptable salts such as alkali metal and other common basic salts or acid addition salts, etc. References to the base substances are therefore intended to include those common salts known to be substantially equivalent to the parent compound and described in the above referenced applications or patents.

The following examples are meant to illustrate the methods for determining critical elements of the invention and are nonlimiting.

EXAMPLE 1

5,7-Dichloro-1,4-dihydro-4-oxo-2-quinolinecarboxylic acid

Results of two studies in mice show that 5,7-dichloro-1,4-dihydro-4-oxo-2-quinolinecarboxylic acid, a NMDA-site glycine antagonist, crosses the blood-brain barrier but returns at a faster rate to the blood by unidirectional efflux. Following intravenous administration of tritiated 5,7-dichloro-1,4-dihydro-4-oxo-2-quinolinecarboxylic acid ([$^3$H]-5,7-dichlorokynurenic acid) to mice, very little penetration and/or retention of radiolabeled material is observed in brain tissue over a 4-hour period. To determine if 5,7-dichloro-1,4-dihydro-4-oxo-2-quinolinecarboxylic acid does not cross the blood brain barrier or penetrates but is rapidly cleared from the brain. A follow-up study is performed in which tritiated 5,7-dichloro-1,4dihydro-4-oxo-2-quinolinecarboxylic acid is injected directly into the cerebral ventricle of mice at two dose levels. By 60 minutes postdose 12% and 83.4% of total radioactivity remains in brain tissue from the initial concentration following administration of a 0.3 and 1.3 mg/kg dose, respectively. The ratio of area under the brain radioactivity curve (5–120 minutes) for the 1.3 mg/kg to 0.3 mg/kg dose is 12, approximately threefold greater than anticipated based on linear kinetics. This data shows 5,7-dichloro-1,4-dihydro-4-oxo-2-quinolinecarboxylic acid is actively transported from brain to blood by a saturable process. Coadministration of probenecid with 5,7-dichloro-1,4-dihydro-4-oxo-2-quinolinecarboxylic acid slows the active transport process and increases the amount and duration of 5,7-dichloro-1,4-dihydro-4-oxo-2-quinolinecarboxylic acid in brain following IV administration to mice brain and the ability of probenecid to block active, unilateral transport out of the brain.

EXAMPLE 2

2,3-Dihydroxy-6-nitro-7-sulfamoylbenzo(F) quinoxaline or NBQX

Adult male CF1 strain mice (18 to 24 g body weight) are obtained from Charles River Laboratories. Mice are allowed free access to food and water prior to testing. Maximal electroshock is performed according to conventional methods (Krall, R. L., et al, Antiepileptic drug development: II. Anticonvulsant drug screening, *Epilepsia* 19:409–428 (1978). Electrical current (50 mA sinusoid at 60 Hz) is applied by metal corneal electrodes for 0.2 sec. This intensity of electrical current is five times the amount needed to produce tonic extensor seizures in untreated mice. Pretreatment of mice with known anticonvulsant drugs prevents tonic extensor seizures in a dose-related manner (Krall, R. L., et al, Antiepileptic drug development: II. Anticonvulsant drug screening, *Epilepsia* 19:409–428 (1978). A drug is prepared for intravenous administration by dissolution in aqueous medium with 0.9% sodium chloride. Probenecid is finely divided with mortar and pestle and suspended in 0.2% carboxymethylcellulose in water and given by intraperitoneal injection 30 minutes before administration of anticonvulsant drugs. (Probenecid (200 mg/kg) followed by intravenous administration of 0.09% sodium chloride vehicle causes no anticonvulsant actions in any of 10 mice.)

That is, groups of ten mice each are pretreated with probenecid (200 mg/kg IP) or saline vehicle. Thirty minutes later each group is given a known anticonvulsant dose of one of several anticonvulsant drugs. The time course of anticonvulsant activity is determined by maximal electroshock testing in groups of mice at various times after administration of the anticonvulsant. Results are expressed as the percentage of mice that failed to have a tonic extensor seizure of hindlimbs (percent of mice protected).

The time course of anticonvulsant action with the known AMPA-type glutamate antagonist NBQX (2,3-dihydroxy-6-nitro-7-sulfamoyl-benzo(F)quinoxaline) is shown in FIG. 1. With only NBQX (25 mg/kg given intravenously) given after saline vehicle, significant anticonvulsant actions are present until 3 minutes (180 seconds) after dosing, but only insignificant anticonvulsant action is seen 15 minutes (900 seconds) after dosing. However, with coadministration of NBQX and probenecid (200 mg/kg), significant anticonvulsant effects are seen 15 minutes (900 seconds), 30 minute (1800 seconds), 1 hour (3600 seconds), and 2 hours (7200 seconds) after dosing but not 4 hours (14400 seconds) after dosing. These results indicate a marked potentiation of anticonvulsant effects of NBQX when it is given in combination with probenecid.

Other CNS behavioral effects of NBQX are also markedly increased by coadministration with probenecid, as evidenced by ptosis, profoundly decreased locomotor activity, greatly delayed righting reflex, and somnolence following the combination of probenecid with 25 mg/kg NBQX but not with administration of 25 mg/kg NBQX and saline.

EXAMPLE 3

Figure 2:
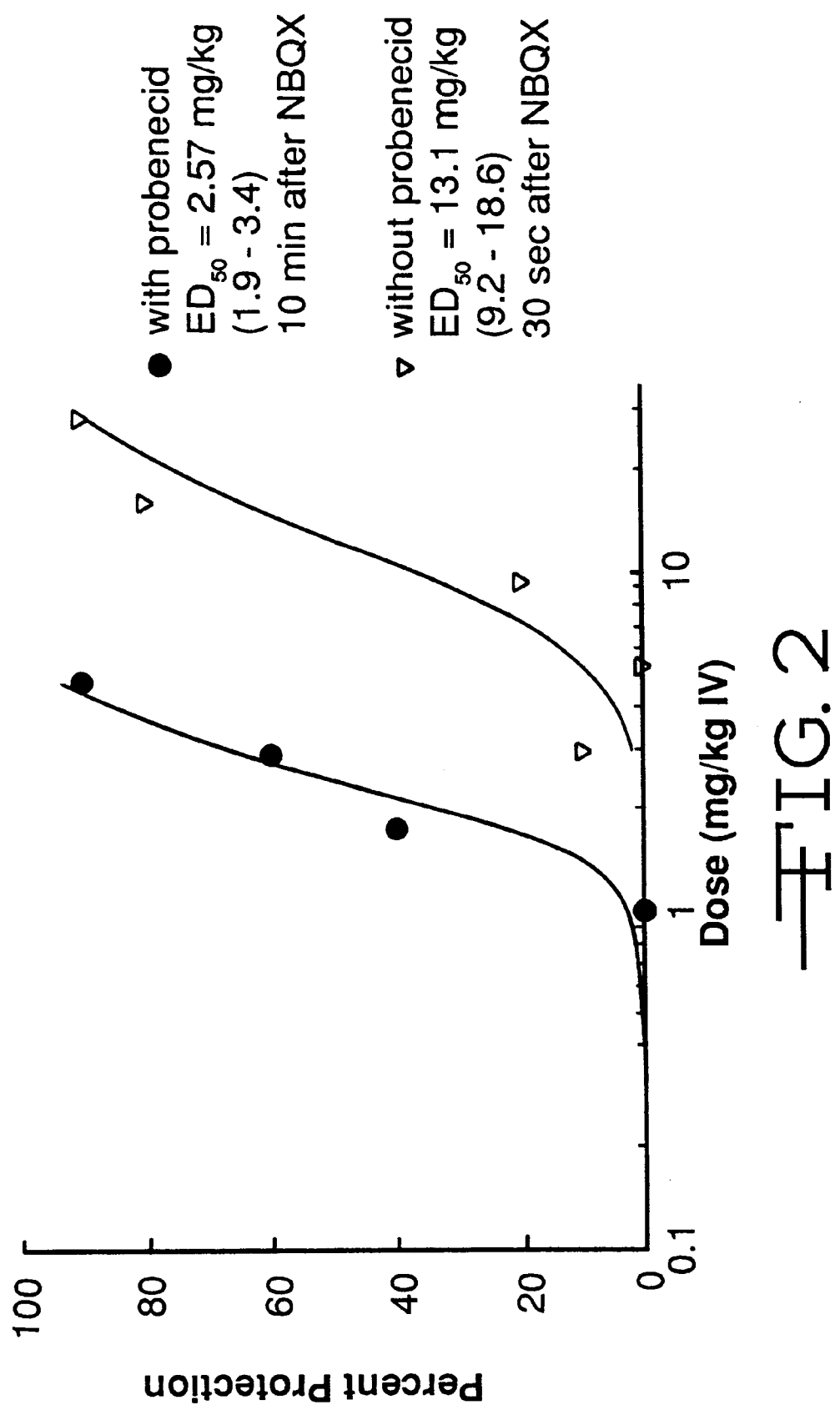
FIG. 2 shows the prevention of tonic extensor seizures from maximal electroshock in mice by NBQX administration with ● and without (▽) combined treatment with probenecid, 200 mg/kg intraperitoneally. The smooth curves are the best fit to the data by probit analysis (J. T. Litchfield and F. Wilcoxon in *Journal of Pharmacology* 96:99–113, 1949). $ED_{50}$ values from probit analysis are shown, along with 95% confidence intervals (in parentheses).

Using procedures identical to those of Example 2, but with administration of several different doses of NBQX, $ED_{50}$ values were determined by probit analysis (J. T. Litchfield and F. Wilcoxon in *Journal of Pharmacology* 96:99–113, 1949), with times of testing chosen at approximately the time of maximal anticonvulsant effect (30 seconds for NBQX alone and 10 minutes for NBQX with probenecid coadministration, from Example 1). Results are shown in FIG. 2 with an $ED_{50}$ value for NBQX alone of 13.1 mg/kg and for NBQX coadministered with probenecid of 2.57 mg/kg. The 95% confidence intervals of $ED_{50}$ values are shown in the figure in parentheses. These values differ significantly (p<0.05), demonstrating a quantitative increase in potency of NBQX of approximately fivefold following probenecid coadministration.

EXAMPLE 4

4-(3-Phosphonopropyl)-2-piperazinecarboxylic acid, hydrochloride

Figure 3:
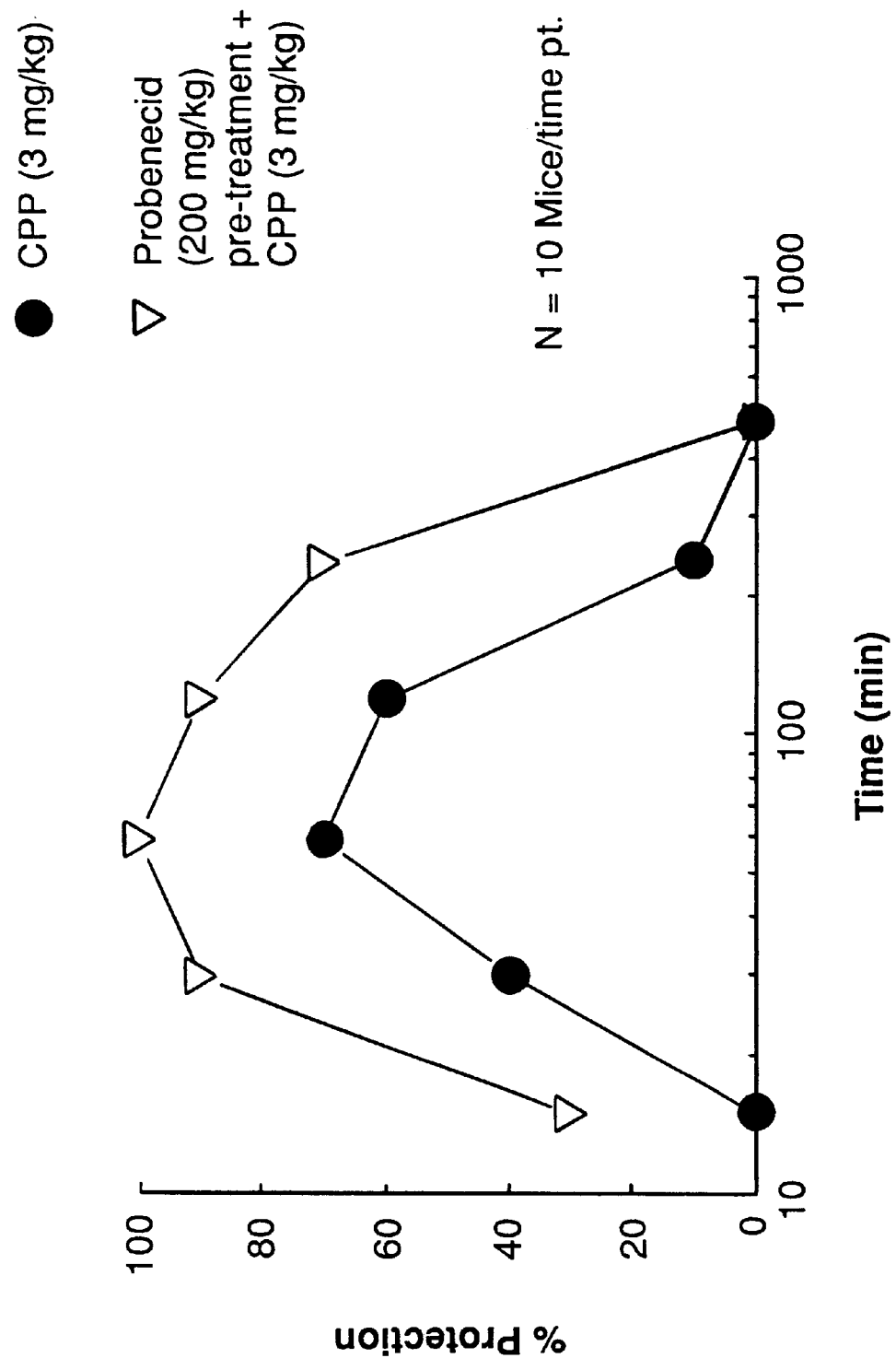
FIG. 3 shows the effect of anticonvulsant action over time of 3 mg/kg, of 4-(3-phosphonopropyl)-2-piperazinecarboxylic acid, CPP administered by intravenous injection in 10 mice as ● and the effect of anticonvulsant action over time of 3 mg/kg of CPP administered by intravenous injection in mice pretreated (30 minutes before injection of CPP) by intraperitoneal injection of 200 mg/kg of probenecid ▽.

In an analogous study with the known NMDA-type competitive glutamate antagonist, CPP, anticonvulsant actions are also increased by coadministration with probenecid, even though to a smaller extent (FIG. 3). The duration of significant anticonvulsant action of 3 mg/kg CPP is increased from 120 minutes (2.0 hours) without probenecid to 240 minutes (4.0 hours) with probenecid. The percentage of mice protected from maximal electroshock seizures is also increased by probenecid coadministration at each time point tested. However, although the extent of the improved effect of probenecid is less with CPP than with NBQX, the effect is still quantitatively greater for the coadministered agents.

EXAMPLE 5

5,7-Dichlorokynurenate

Figure 4:
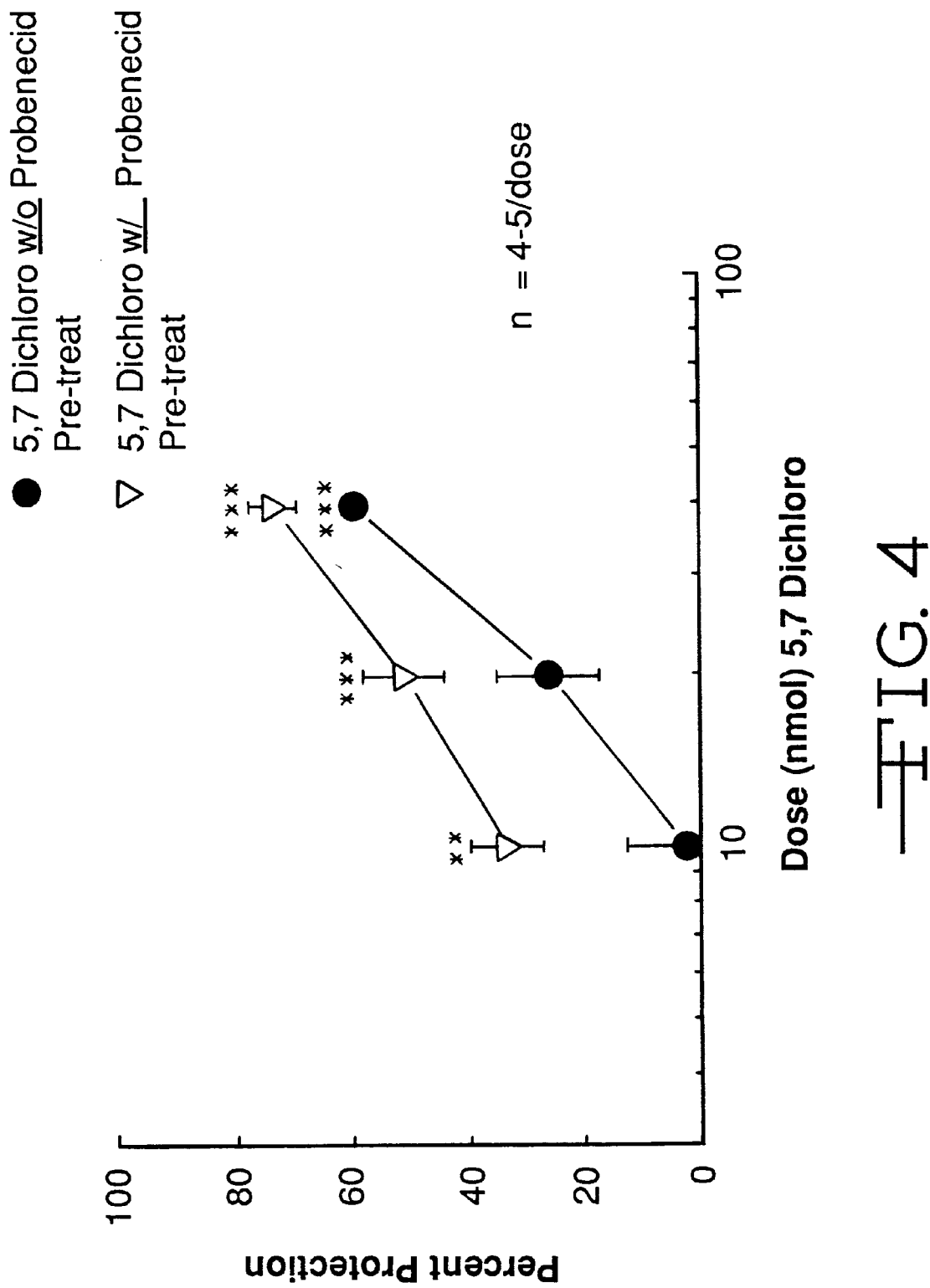
FIG. 4 shows the percent of the brain protected by 5,7-dichlorokynurenic acid (co-injected) on NMDA-induced brain injury in rat without pretreatment by probenecid shown as a nanomolar dose by ● and with ip pretreatment with 200 mg/kg of probenecid at 30 minutes before injection shown as ▽.

The neuroprotective action of 5,7-dichlorokynurenate is assessed using an animal model with young rats. Seven-day-old albino rat pups of either sex are anesthetized and given N-methyl-D-aspartate (NMDA) by injection with a fine hypodermic needle into the right posterior corpus striatum. Four days later, the degree of brain damage from NMDA injection is assessed by comparing wet weights of the injected cerebral hemispheres. Methods are similar to those of J W McDonald et al. in *Experimental Neurology* 106:289–296 (1989) except that 15 nmol of NMDA is used rather than 25 nmol as in the McDonald method. The neuroprotective action of 5,7-dichlorokynurenic acid is assessed by injecting it directly into the striatum of the brain in combination with NMDA. As shown in FIG. 4, the neuroprotective action of 5,7-dichlorokynurenic at three different doses is significantly enhanced by pretreatment of rat pups with 200 mg/kg probenecid. Administration of probenecid alone did not alter the extent of brain damage in comparison to untreated animals.

These results support the present invention showing that probenecid pretreatment prevents the transport of 5,7-dichlorokynurenate out of brain tissue and thus increases its neuroprotective action.

We claim:

1. A method of treating a neurodegenerative disease, the method comprising administering to a patient having a neurodegenerative disease a pharmaceutical composition that comprises:
   a. an amount of a kainate excitatory amino acid antagonist effective to treat the disease;
   b. an amount of a uricosuric agent effective to inhibit unidirectional efflux of the kainate excitatory amino acid antagonist through the blood brain barrier; and
   c. a pharmaceutical carrier.

2. The method of claim 1 wherein the neurodegenerative disease is stroke.

3. The method of claim 1 wherein the uricosuric agent is probenecid.

4. The method of claim 3 wherein the amount of probenecid is about 500 mg.

5. A pharmaceutical composition which comprises:
   a. an amount of a kainate excitatory amino acid antagonist effective to treat the disease;
   b. an amount of a uricosuric agent effective to inhibit unidirectional efflux of the kainate excitatory amino acid antagonist through the blood brain barrier; and
   c. a pharmaceutical carrier.

6. The pharmaceutical composition of claim 5 wherein the uricosuric agent is probenecid.

7. The pharmaceutical composition of claim 6 wherein the amount of probenecid is about 500 mg.

8. A method of treating epilepsy, schizophrenia, anxiety or pain which comprises:
   a. an amount of a kainate excitatory amino acid antagonist effective to treat the disease;
   b. an amount of a uricosuric agent effective to inhibit unidirectional efflux of the kainate excitatory amino acid antagonist through the blood brain barrier; and
   c. a pharmaceutical carrier.

9. The method of claim 8 wherein the uricosuric agent is probenecid.

10. The method of claim 9 wherein the amount of probenecid is about 500 mg.

* * * * *